(12) United States Patent
Fogelman et al.

(10) Patent No.: US 8,877,051 B2
(45) Date of Patent: Nov. 4, 2014

(54) TIME DELAY FOR SAMPLE COLLECTION IN CHROMATOGRAPHY SYSTEMS

(75) Inventors: Kimber D. Fogelman, Hockessin, DE (US); Edwin E. Wikfors, Landenberg, PA (US); Rui Chen, Newark, DE (US)

(73) Assignee: Waters Technologies Corporation, Milford, MA (US)

( * ) Notice: Subject to any disclaimer, the term of this patent is extended or adjusted under 35 U.S.C. 154(b) by 2391 days.

(21) Appl. No.: 11/490,499

(22) Filed: Jul. 21, 2006

(65) Prior Publication Data

US 2009/0050568 A1 Feb. 26, 2009

(51) Int. Cl.
*G01N 30/82* (2006.01)

(52) U.S. Cl.
CPC ....................................... *G01N 30/82* (2013.01)
USPC .......................... 210/198.2; 210/143; 210/656

(58) Field of Classification Search
CPC ....................................................... G01N 30/82
USPC ........................ 210/198.2, 635, 656, 659, 143
See application file for complete search history.

(56) References Cited

U.S. PATENT DOCUMENTS

| | | | | |
|---|---|---|---|---|
| 3,304,159 A | * | 2/1967 | Hinsvark | 436/115 |
| 4,003,243 A | * | 1/1977 | Blu et al. | 73/61.52 |
| 4,236,404 A | * | 12/1980 | Ketchum et al. | 73/19.02 |
| 4,500,432 A | * | 2/1985 | Poole et al. | 210/659 |
| 4,532,043 A | * | 7/1985 | Prud'homme et al. | 210/635 |
| 5,234,586 A | * | 8/1993 | Afeyan et al. | 210/198.2 |
| 5,306,426 A | * | 4/1994 | Afeyan | 210/635 |
| 5,322,626 A | * | 6/1994 | Frank et al. | 210/634 |
| 5,968,367 A | | 10/1999 | Quinn et al. | |
| 6,106,710 A | | 8/2000 | Fischer et al. | |
| 6,406,633 B1 | | 6/2002 | Fischer et al. | |
| 6,997,031 B2 | | 2/2006 | Gilby et al. | |
| 7,086,279 B2 | * | 8/2006 | Gilby et al. | 73/61.57 |
| 2001/0013494 A1 | * | 8/2001 | Maiefski et al. | 210/656 |
| 2003/0019812 A1 | * | 1/2003 | Berger et al. | 210/656 |

* cited by examiner

*Primary Examiner* — Ernest G Therkorn
(74) *Attorney, Agent, or Firm* — Waters Technologies Corporation

(57) ABSTRACT

A system and process for chromatography that uses a chromatography column to separate components from a sample received into the column in a mobile phase flowstream and places a second chromatography column between a detector and a collection system that compensates the timing of fraction collection for a delay caused by processing the collection signals generated by the detector. The device and process of the preferred and alternative embodiments add a delay into the flowstream of a chromatographic system, such as LC, HPLC, and SFC. Sample fractions are collected from sample component concentration peaks based upon the chromatographic elution of the sample components.

5 Claims, 5 Drawing Sheets

TIME DELAY FOR SAMPLE COLLECTION IN CHROMATOGRAPHY SYSTEMS

FIELD OF THE INVENTION

The present invention relates to a compound separation and collection system, and more specifically compound detection and timing for collection in a chromatography system.

BACKGROUND OF THE INVENTION

In the technology of separation of compounds using chromatography, analyzing and collecting separated fractions of chemical compounds have advanced to processes and systems that vary greatly in process, instruments, and production capability. Liquid chromatography uses a fluid, called a mobile phase, that is pumped through a chromatography separation column, called the stationary phase. A liquid sample containing one or more chemical compounds is injected into the mobile phase flowstream at the head of the column. Different compounds in the sample are delayed in the stationary phase for different time periods.

The separated compounds exit the column according to different retention times. These separated compounds can be detected and graphed as a "peak" of the injected sample. Purified samples can then be collected that correspond to the peak in the flowstream. If constant temperature, pressure, flowrate, and injection sample composition is maintained in the system, then repeated injections of the compounds to separate into the column can produce repeatable peaks eluting from the column. These eluted peaks contain purified analytes of interest that can be collected through automated timing of a collection system.

The parameters and instruments of the chromatography system can be adjusted in order to optimize the speed, efficiency, and accuracy of analyte collection. An advancement of LC is HPLC (High Performance Liquid Chromatography), which uses 20 mm to one inch diameter columns with flowrates optimized at 20 to 30 ml/min. While process and collection speeds are faster than LC, drawbacks to HPLC include high waste solvent production and slow effective process time for samples due to removal of solvent and water from collected sample fractions.

In FIG. 1, a pump system 10 feeds a mobile phase under pressure into packed chromatography column 14. Injection valve 12 injects sample at the head of column 14. The efficiency of the separation of sample components inside packed column 14 is affected by pressure and temperature inside the column, length and diameter of the column, flowrate of the system, mobile phase composition, and composition and volume of the stationary phase inside the column. Collection system 16 can retain components of interest that correspond to detected fractionated peaks in the flowstream after column 14. Components that elute out of the column 14 can be detected by a detector 18 that receives a flowstream 20 split off from the primary flowstream 22. Collection system 16 collects purified fractions using a valve system 24 that is timed by a computer controller 26 to direct the flowstream 22 into collection system 16 when the flow corresponding to a peak reaches the valve 24. Flow not directed to collection system 16 passes to waste stream 28 or additional system processes. Controller 26 receives data from, and sends control signals to, pump 10, detector 18, and valve 24.

From the time a sample is injected into the column 14 at injector 12, each eluted component that is desirable for collection passes from the column 14 into the collection system 16 according to a timing calculation by controller 26 from the point of detection. This calculation accounts for the time for the detector 18 to analyze and process the flowstream, and the time for the peaks of eluted components to reach collection system 16. These timing factors are tracked by controller 26 that turns the valve 24 at the proper time to direct a fraction into the collection system 16 for the approximate length of time of the peak in the flowstream.

The detector 18 can be of two types, destructive or non-destructive. Ultraviolet detectors are commonly used non-destructive types and mass spectrometers are commonly used destructive types of detectors. Both types must be able to accurately detect the eluted compounds in the flowstream faster than the compounds will reach the collection system, otherwise some type of delay in the flowstream must be added. The detector can analyze and use sensors to detect the eluant compounds in the flowstream and send the signals to controller 26, which then triggers the valve 24 to time the direction of the flowstream into collection system 16 with the detected components. Detector 18 is upstream of the collection system and can be either in-line with the flowstream or split off 20 from the main flowstream line. A "splitter" divides a percentage of the entire mobile phase flow to the detector 18, while the remaining flow continues towards the collection system 16. A destructive tester 18 is usually installed on a split in the mobile phase flowstream.

U.S. Pat. No. 6,406,633 to Fischer describes timing of a fraction collection system after detection of sample fraction peaks. The timing calculation is determined empirically by injecting a calibrant into the mobile phase and detecting the calibrant using an upstream mass spectrometer split from the flowstream and a second downstream detector. The time of detection in the first detector and the time of detection of the same components in the second detector in the waste stream gives and actual time delay between those two points in the flowstream. In U.S. Pat. No. 6,997,031 to Gilly describes using configuration on an LC system to calibrate the system for delay and accurate fraction collection. The patent describes a mass spectrometer split off of the main flowstream prior to the collection system and a UV detector downstream of the collection system. Neither reference discloses, or even addresses, the problems associated with a delay caused by sensing and processing of an upstream detector and the travel time for a flowstream on a split to the detector prior to a collection system.

Although HPLC is an advancement over LC, similar problems exist for collection of sample fractions. Further, even more drawbacks exist to the current use of preparative HPLC. Elution periods ranging from several minutes to hours are necessary for each sample. Even in optimal conditions only a small fraction of the mobile phase contains components of interest. This can lead to very large volumes of waste mobile phase being generated in normal operation of the system.

For many applications, an alternative separation technology called supercritical fluid chromatography (SFC) has advanced past other chromatography technologies. SFC uses highly compressible mobile phases, which typically employ carbon dioxide ($CO_2$) as a principle component. In addition to $CO_2$, the mobile phase frequently contains an organic solvent modifier, which adjusts the polarity of the mobile phase for optimum chromatographic performance. Since different components of a sample may require different levels of organic modifier to elute rapidly, a common technique is to continuously vary the mobile phase composition by linearly increasing the organic modifier content. This technique is called gradient elution.

SFC has been proven to have superior speed and resolving power compared to traditional HPLC for many applications.

This results from the dramatically improved diffusion rates of solutes in SFC mobile phases compared to HPLC mobile phases. Separations have been accomplished as much as an order of magnitude faster using SFC instruments compared to HPLC instruments using the same chromatographic column. A key factor to optimizing SFC separations is the ability to independently control flow, density and composition of the mobile phase over the course of the separation. SFC is finding significant advantages in the separation of enantiomers and is supplanting normal-phase HPLC for performing chiral separations.

A problem in all of the above-referenced separation technologies, but especially HPLC and SFC is when the chromatographic system is combined with a mass spectrometer on a split after the column but upstream from a collection system. The signal that is generated by the mass spectrometer, that indicates whether there is peak of a fraction ready to be collected, is generally delayed in time. The delay can last from a few hundred milliseconds up to ten seconds or more. Causes for the delay include operations for sensing, analyzing, and processing time in the mass spectrometer as well as the computer processing for a controller. These processing delays can be caused by complexity of the compound that creates the signal for the spectrometer to analyze, the complexity of rules for analyzing and presenting the signal, complexity or interference of other signals in the system caused by background interference from other components in the flowstream, and speed of the processor and bus in the instruments and in the controller. Other delays include transmission of the flowstream from the primary flow line 22 to the split detector 18 in flow line 20. In general, a signal from a detector may not vary widely for a particular sample run. However this is not always the case, and furthermore when beginning a sample run the delay is an unknown parameter that can adversely affect collection of the components. Changes in delay can be caused by numerous factors in the system that include flowrate and pressure, sample and mobile phase composition, and column 14 efficiency.

In LC and HPLC, a traditional system modification to compensate for this delay is to install a loop of tubing that is termed a "delay loop" in the industry. The delay loop 30, illustrated in FIG. 1, is placed after the split 20 to the detector 18 and prior to the flowstream reaching collection system 16. The delay loop 30 passes the primary flowstream through its coiled tubing. The length of the tubing adds a known amount of time after the detector has detected the component peak for the peak fraction to reach a valve decision point 24 that directs the flow to the collection device 16, a waste stream 28, or a different downstream process. Since a chromatography system flow typically includes an incompressible fluid, the delay can be calculated by volume divided by the flowrate.

A special problem in SFC in compensating for delay is that linear flowrates through tubes are generally significantly higher than HPLC and LC due to the extremely high flowstream pressures in SFC. The same problems apply to SFE. The use of wide-bore tubing in SFC is undesirable because of the problems associated with dispersion of the peak that would occur after the detector has defined the peak in the stream. Using small-bore tubing in SFC creates problems as well, which includes adding up to 20 or 30 meters of tubing for a delay compensation since the flowstream velocity is measured on the order of meters/second. Further, the extremely fast flowstream for a great distance can itself cause pressure and dispersion problems of the separated fraction in the flowstream. Further, on the low pressure side downstream of a BPR 37, the SFC flowstream undergoes up to a 500:1 expansion of the compressed gas in the mobile phase that is nonlinear throughout the tubing. The flowrate for this part of the flowstream is virtually impossible to calculate as the stream changes its composition within the tube.

SUMMARY OF THE INVENTION

The device and process of the preferred and alternative embodiments add a delay into the primary flowstream of a process flowstream that is used for separation and collection of compounds in a mobile phase, such as LC, HPLC, and SFC systems. In systems that use a split line and detector after an initial separation of compounds by a chromatography column, a packed chromatography column is placed in the flowstream between the split and a collection system. Compounds are collected in these systems based prediction of when a certain compound will exit the separation column and the time for flowing to the collection device.

The preferred and alternative embodiments compensate for the split flowstream travel time and processing delays associated with a split stream detector so that the primary flowstream containing the separated compounds will reach the. Instead of a delay loop into a flowstream.

BRIEF DESCRIPTION OF THE DRAWINGS

For a better understanding of the nature of the present invention, its features and advantages, the subsequent detailed description is presented in connection with accompanying drawings in which.

DETAILED DESCRIPTION OF THE INVENTION

Figure 1:
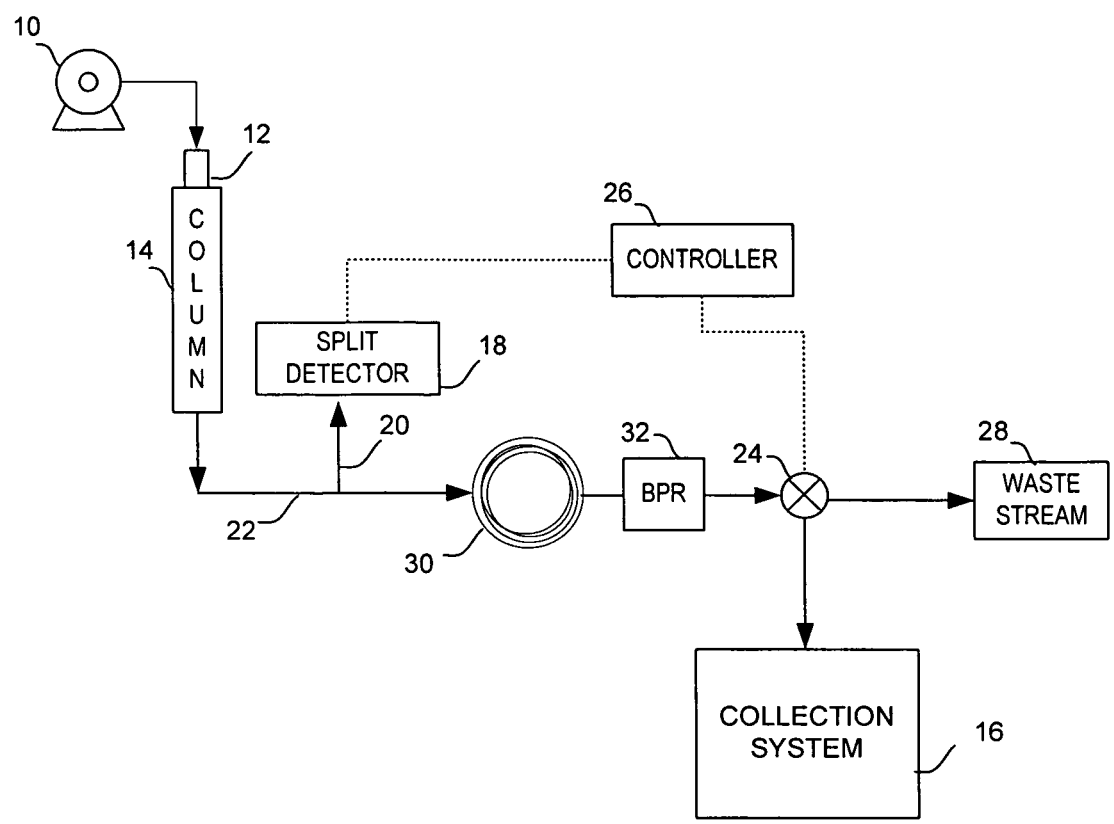
FIG. 1 illustrates components of prior art chromatography systems.
Figure 2:
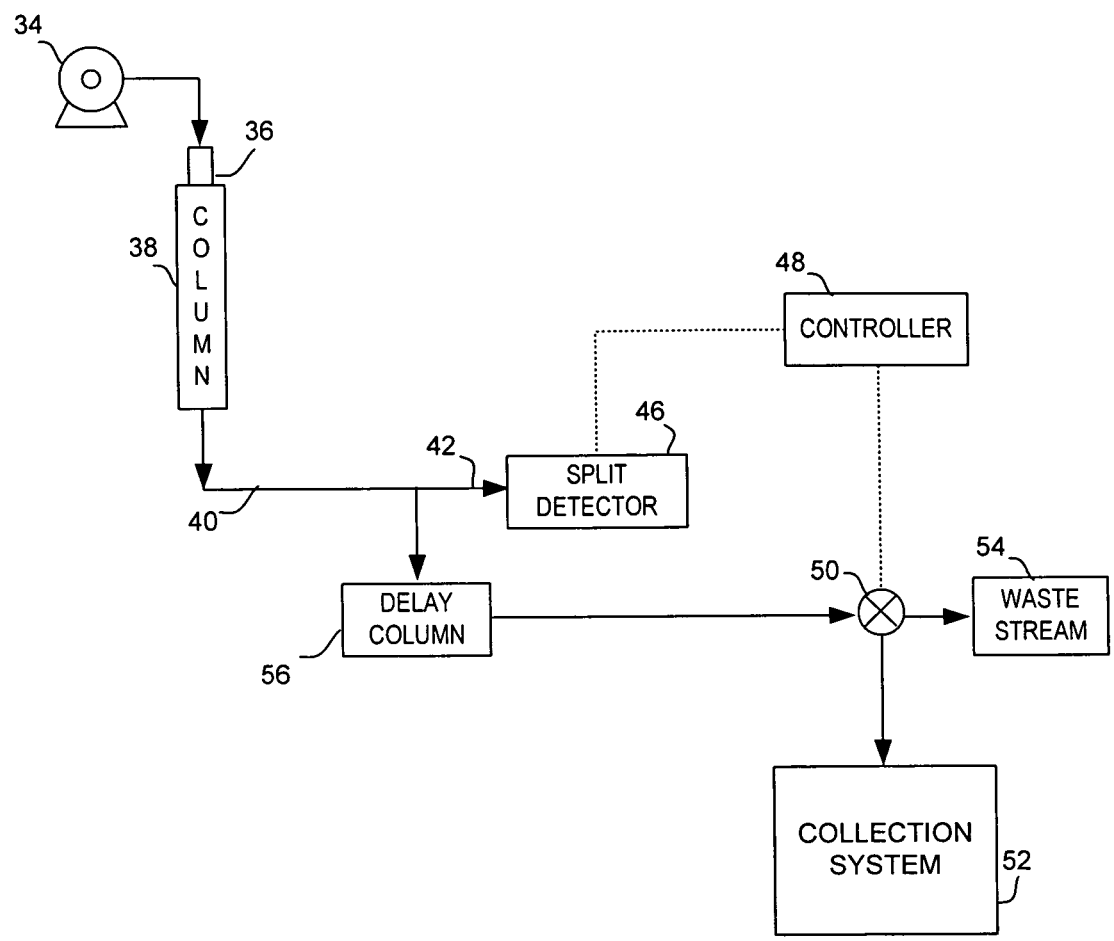
FIG. 2 illustrates an exemplary chromatography system implementing the preferred embodiment.

The preferred and alternative embodiments are used in the collection process of sample components, commonly called fractions, that have eluted from a chromatography column. The preferred embodiment is a method and system of using a chromatography packed column with known phase and flow parameters that adds delay of the flowstream prior to entering a collection system directional valve or other re-directing mechanism. In FIG. 2, an exemplary chromatography system capable implementing the preferred embodiment is illustrated. The system may use liquid chromatography (LC), high performance liquid chromatography (HPLC), supercritical fluid chromatography, or supercritical fluid extraction technology.

The preferred embodiment uses pump system 34 may include multiple pumps with mixtures of modifier liquid and gas, depending upon the type of chromatography system used. Pump 34 feeds a mobile phase under pressure into chromatography column 38. Injection valve 36 provides the means to inject a liquid sample S106 into the flowstream at the head of column 38 for separation S108 of sample analytes, or components, according to each component's retention time in the column 38. Collection system 52 can retain analytes of interest that correspond to peaks in the flowstream after column 38. Sample components elute out of the column 38 and are analyzed S110 by a detector 46 that receives a flowstream 42 that is split off from the primary flowstream 40. Detector 46 is typically a destructive detector such as a mass spectrometer. Flow split off to detector 46 typically ranges from approximately ¼ down to ¹⁄₁₀₀₀th of the primary flowstream's 40 volumetric flowrate.

Collection system 52 collects purified fractions of the injected sample when a valve system 50 directs the flowstream into the collector 52 according to control signals received from controller 48. Direction of valve 50 depends upon timing in the system when a peak of sample fractions reach the valve 50. Flow not directed to collection system 16 passes to waste stream 54 or additional system processes. Controller 48 receives data from, and sends control signals to detector 46 and valve 50.

When the chromatographic system is combined with a detector either in-line or on a split after the column, but upstream from a collection system, the signal, which is generated by the detector indicating whether there is peak of a fraction ready to be collected, is generally delayed in time. The delay can last from a few hundred milliseconds up to ten seconds or more. Causes for the delay include processing time in the detector 46 as well as the computer processing for controller 48. These processing delays can be caused by complexity of the signal that the spectrometer and controller analyze, the complexity of rules for analyzing and presenting the signal, complexity or interference of other signals in the system caused by background interference from other components in the flowstream, and speed of the processor and bus in the instruments and controller, among others. Controller 48 and/or empirical observations can determine the length of the delay S112.

To compensate for the delay caused by processing the signals generated by detector 46, instead of a delay loop 30 as discussed in the prior systems, the preferred embodiment uses a packed chromatography column 56 termed herein a "delay column." The delay column is placed S114 in the flowstream 40 between the column 38 and the collection system 52. Delaying the mobile phase with a packed column placed in this configuration (shown in FIG. 2) overcomes the problems associated with tubing and length of delay loops that disperse the sample fractions in the flowstream, as described above. It is well known to one skilled in the art what the predicted dispersion of the mobile phase through a particular specified column according to the column's stationary media and dimensions. Using a column 56 that is intentionally specified as non-retentive to the sample components in the flowstream causes minimal dispersion of the components and more importantly lowers the flowrate in the mobile phase to approximately match at delay associated with signals from split detector 46.

An exemplary delay column could be specified as a packed chromatography column. Generally, a 15 cm by 2.1 cm column receiving a flowrate of 50 ml/min has a delay of approximately 45 seconds. The delay time induced on the system decreases linearly with length of a column. For example, a 15 second delay in delay column 56 could be achieved for a mobile phase flowrate of 50 ml/min using a column with dimensions of 5 cm length and 2.1 cm diameter. If the chromatography system uses a 200 ml/min flowrate, the retention time decreases linearly with flowrate. Therefore, if the flowrate is doubled, then the column retention time is cut in half. The exact specifications for an implementation of delay column 56 should be chosen based upon an expected range of flowrates and composition of injected sample. The dimensions and stationary media of the delay column 56 are chosen for specific system, flowrate, and flowstream demands and composition so that a delay is introduced into the mobile phase flowstream that compensates for delay introduced from adding a split stream 42 and an upstream detector 46.

It should be noted that the delay column 56 does not create a variable restriction of the flowstream from the column 36. Instead the delay column 56 produces in the flowstream a similar delay for a preponderance of the compounds in the mobile phase flowstream that are separated by the first column 38. The timing for collection of the separated compounds in the flowstream is based upon the time delay to the collection system from column 38. The injection samples of the compounds themselves are not varied to create an additional variable of collection. The preferred method and system provides a delay in the mobile phase flowstream that provides a known dispersion with a known broadening of the peak flow that is a significant improvement over the problems associated with delay loops. In addition to the delay created in the second column 56 that corresponds to the delay in the flowstream of compounds separating through the first column 38, the second column can add a minimal delay of the compounds in the flowstream ranging from approximately ten seconds or less. The times for delay of the split stream include the time for a compound to travel split flow line 42 and reach the split detector 46 and the sensing and processing by the spectrometer and the computer processors in the detector and controller as described previously. These times can be factored into the timing calculation for collection of a peak by the controller 48.

The type of column used as a delay column 56 can vary according to application in the process system. However, some guidelines for the column 56 should be to have the packed media bed manufactured with a non-polar surface area with packing material that will not or will not significantly broaden the peaks of the compounds in the flowstream that were separated by the first column 38. Broadening of the peaks in the flowstream would work against the goal of collecting each peak using the prediction of the collection window of a peak flowing out of the first column 38 reaching the collection system 52.

Figure 3:
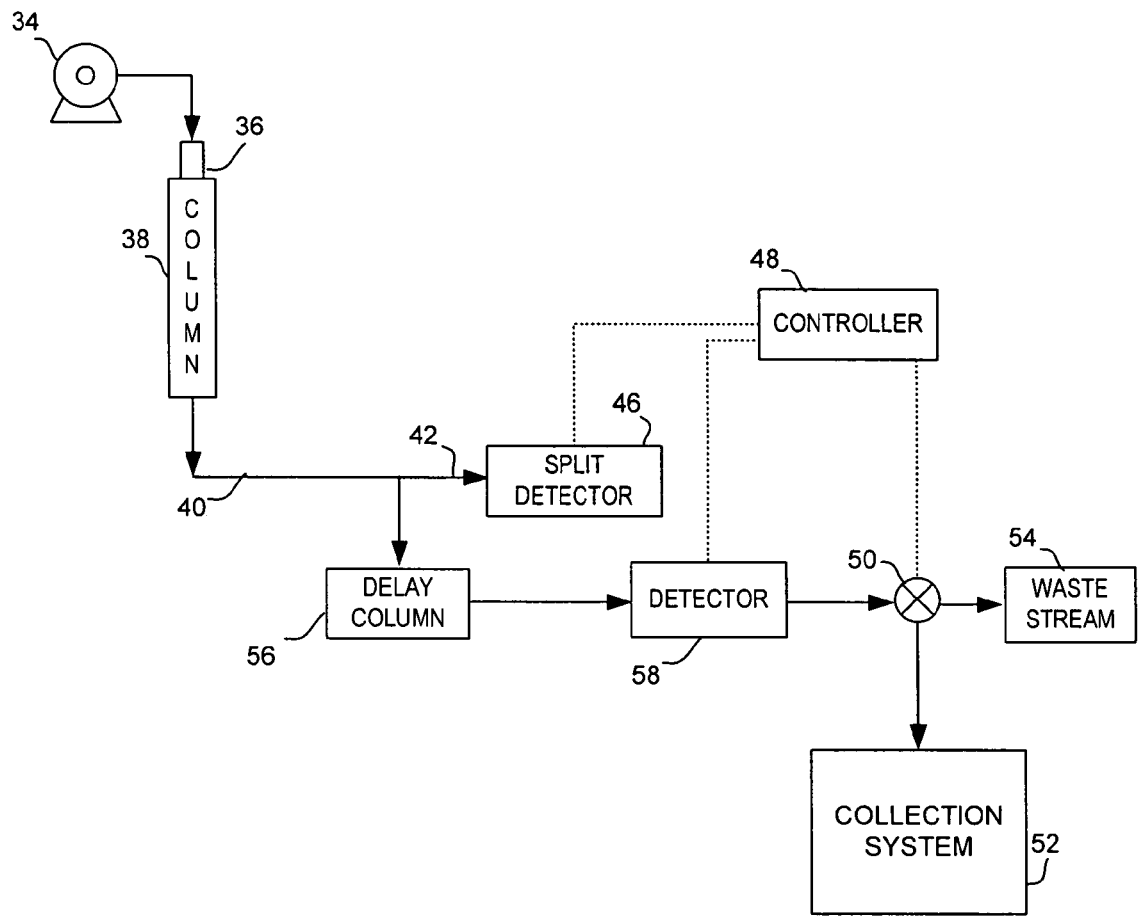
FIG. 3 illustrates an exemplary chromatography system implementing the alternative embodiment.
Figure 4:
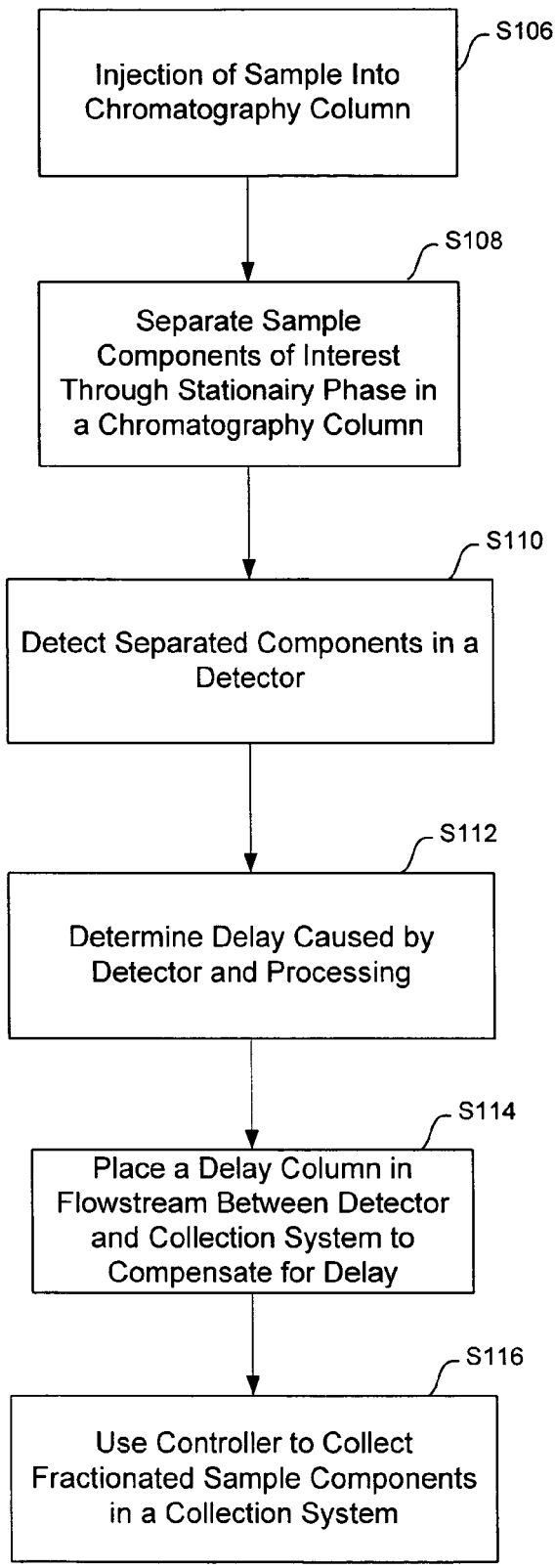
FIG. 4 illustrates a flowchart of a process of the preferred and alternative embodiments.

In FIG. 3, an alternative embodiment to the preferred system and process illustrates the chromatographic system shown in FIG. 2 but with a second detector 58 placed in flowstream 40 between the outlet of delay column 56 and valve 50. Detector 58 is preferably a non-destructive detector such as an ultraviolet detector that allows the flowstream 40 to pass through the detector without dispersing the eluted sample components. Detector 58 will detect fractionated sample components in real-time, which is some time period prior to split detector 46. The controller 48 analyzes the signals from detector 58 to determine in advance what eluted components are to be expected at detector 46 and the time delay before they will arrive. For example, controller 48 may determine that a signal of components analyzed by first detector 58 is received three seconds prior to the final processed signal of the analyzed components from detector 46. The two signals from detectors 46 and 58 are correlated in controller 48 as resulting from the same sample fractions elute from the column 38. Any time delay from detector 58 is correlated to the time delay from detector 46 in order to determine a delay period in the flowstream that may be compensated for using a properly-specified delay column 56. After sample fractions and mobile phase flows through column 56, valve 50 is triggered S116 by controller 48 to direct the flowstream into collection system 52. The signal to direct valve 50 is then triggered by detection of sample fractions in the detector 58 instead of split detector 46.

Figure 5:
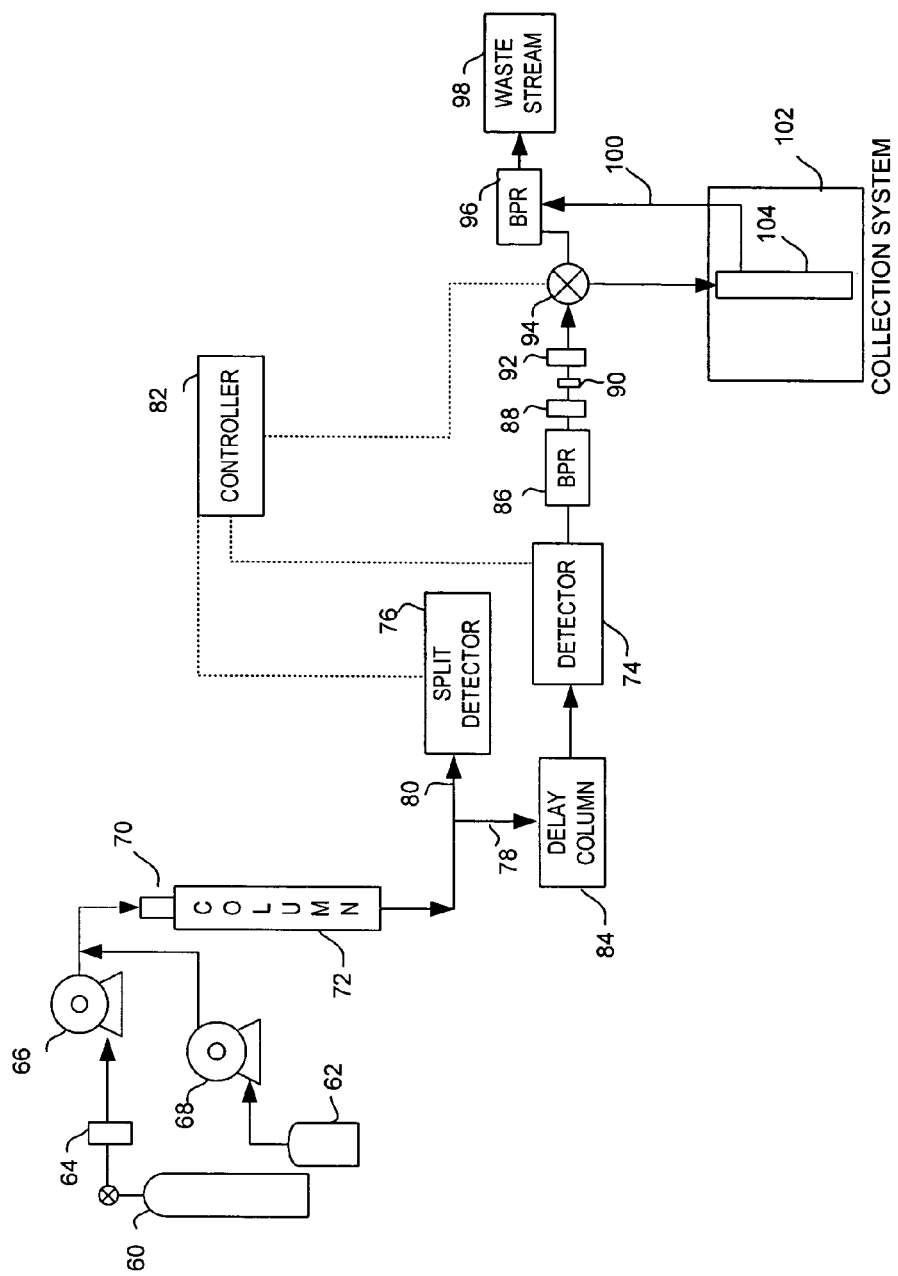
FIG. 5 illustrates an exemplary supercritical fluid chromatography system that can implement the preferred and alternative embodiments.

FIG. 5 illustrates an implementation of the preferred and alternative embodiments of the present invention comprising one type of process stream fed from a supercritical fluid chromatography (SFC) or supercritical fluid extraction (SFE) system. In general, dissolved samples carried through an SFC system also remain dissolved in the liquid organic modifier phase. The principle that simple decompression of the mobile phase in SFC separates the stream into two fractions has great importance with regard to use the technique in a preparative manner. Removal of a gaseous carbon dioxide ($CO_2$) phase, which constitutes 50% to 95% of the mobile phase during normal operation, greatly reduces the liquid collection volume for each component and thereby reduces the post-chromatograhic processing necessary for recovery of separated components.

A first flow stream of a highly compressed gas, compressible liquid, or supercritical fluid could include many compounds, liquid or gas, that could be used in the first flow stream but is preferably composed of liquefied carbon dioxide ($CO_2$) gas from cylinder 60. High pressure transfer tubing connects $CO_2$ source 60 to pump 64. Gas from tank 60 may be cooled through line chiller 64 prior to being compressed in pump 66. The second flow stream is supplied from a relatively incompressible liquid, which is preferably a compound such as methanol that is supplied from modifier supply tank 62. The system uses two SFC-grade or modified reciprocating pumps that can supply adequate pressures and flow rates. Pump 68 supplies modifier flow from tank 62 under pressure to mix with flow stream from pump 66 prior to entering packed chromatography column 72 at a controlled mass-flow rate.

The SFC system in the alternative embodiment can provide for flows of approximately 20 to 100 ml/min total flow ($CO_2$ plus modifier flow) in the highly compressed state from the pumping system. However, flowrates for alternative embodiments and SFC systems could range up to orders of magnitude higher or lower through adjustment or substitution of system hardware and flow parameters. Packed column 72 receives sample injection at its head from injector 70, where a sample is injected into the flowstream. After fractionation of the sample occurs in the column 72, the elution mixture passes through a split flowstream 80 to a split detector 76. The primary flowstream 78 continues through backpressure regulator (BPR) 86 and expanded mobile phase exits the BPR 86 at a velocity of approximately two to five times the flow velocity upstream of BPR 86 and under pressure of, for example, approximately twenty to forty bars. Variations in the expansion occur as a result of the changing modifier solvent concentration from 2.5 to 50 percent over the course of a separation.

From BPR 86, the flowstream passes one or more heaters that may be mounted in series to thermally condition the mobile phase and to boil $CO_2$ out of the elution fluid due to evaporation of $CO_2$ from the flowstream, while preventing dry ice from forming in the flow lines and devices. In FIG. 5, evaporator heater 88 and a trim heater 92 are mounted in series after the BPR 86 and an orifice 90 may be placed between the heaters.

A controller 82 controls the various instruments and sensors in the system and receives a signal from detector 76 that triggers valve 94 to direct the flowstream into collection system 102 when eluted sample fractions reach valve 94. Sample fractions may be directed by valve 94 into one or more collection containers 104, each of which have a gas phase vent line 100 connected to a second BPR 96 that maintains a pressure within container 104 allowing for gentle separation of liquid phase from gas phase within the container 104. Waste gas or waste flowstream components are directed through waste stream 98.

To create a delay in the flowstream 78 that compensates for the delay caused by signals generated from detector 76, instead of a delay loop 30 as discussed in the prior systems, the alternative embodiment uses "delay column" 84. The delay column 84 is placed in the flowstream 78 between the column 72 and BPR 86. Delaying the mobile phase with a packed column placed downstream of column 72 but still on the high pressure side of BPR 86 overcomes the problems associated with tubing and length of delay loops corrupting the eluted sample fractions in the flow stream, as described above. Using a column 84 that is intentionally specified as non-retentive to the sample components in the flowstream causes minimal dispersion of the components and more importantly lowers the flowrate in the mobile phase to approximately match at delay associated with the processing of signals from split detector 76.

The SFC system may alternatively use a second detector 74 placed on flowstream 78 between the outlet of column 84 and BPR 86. Detector 78 is preferably a non-destructive detector such as an ultraviolet detector that allows the flowstream 72 to pass through the detector without dispersing the eluted sample components. Detector 74 will detect fractionated sample components in real-time, which is some time period prior to split detector 76 detecting the same components in split flow 80. The controller 82 correlates the signals from detector 74 with split flow detector 76 to determine in advance what eluted components are to be expected at detector 76 and the time delay before they will arrive. For example, controller 82 may determine that a signal of components analyzed by first detector 74 is received three seconds prior to the signal of the analyzed components from second detector 76. The two signals from detectors 74 and 76 are correlated in controller 82 as resulting from the same fractions of components that have eluted from the column 72 after an injection, then the time delay from detector 76 is added to the time delay from detector 74 in order to determine how much delay in the flowstream is required in delay column 84. After the delay is compensated for in column 84, then valve 94 is triggered to direct the flowstream to collection system 102 by the detection of the sample fractions in the first upstream detector 74 instead of detector 76.

One skilled in the art will appreciate that the present invention can be practiced by other than the described embodiments, which are presented for purposes of illustration and not limitation, and the present invention is limited only by the claims that follow.

What is claimed is:

1. A supercritical fluid chromatography system that uses a mobile phase flowstream containing a liquefied gas or supercritical fluid under pressure mixed with a liquid at or near atmospheric pressure, the system comprising:
   a first chromatography column in fluid connection with a mobile phase flowstream;
   a detector downstream from the column and upstream from a collection system;
   a second chromatography column that is non-retentive to components in the flowstream, downstream of the detector, that compensates for a time delay associated with using the detector;
   a controller, operatively connected to the detector; and
   a valve, placed in the flowstream downstream of the detector, wherein the controller processes the signals from the detector and controls the valve to direct the flowstream into a collection system.

2. The system of claim 1, wherein the detector is located on a flowstream split off from a primary flowstream from the first column.

3. The system of claim 2, wherein the second column compensates for a delay caused by the split flowstream to reach the detector.

4. The system of claim 1, wherein the second column compensates for a delay caused by processing the signals from the detector.

5. The system of claim 1, further comprising: a second detector, operatively connected to the controller and placed in the flowstream between the second chromatography column and the collection system, that detects the separated sample components in the flowstream.

* * * * *